United States Patent
Lantsov et al.

(10) Patent No.: US 12,350,013 B2
(45) Date of Patent: Jul. 8, 2025

(54) SPECTROMETER INCLUDING TUNABLE ON-CHIP LASER AND SPECTRUM MEASUREMENT METHOD

(71) Applicant: SAMSUNG ELECTRONICS CO., LTD., Suwon-si (KR)

(72) Inventors: Alexey Dmitrievich Lantsov, Lobnya (RU); Alexey Andreevich Shchekin, Moscow (RU); Sergey Nikolaevich Koptyaev, N.Tagil (RU); Alexey Grigorievich Anikanov, Moscow (RU); Maksim Vladimirovich Ryabko, Dolgoprudny (RU); Pavel Alexandrovich Ivshin, Balashiha (RU); Vasiliy Viktorovich Grigoriev, Moscow (RU); Tatyana Igorevna Kopysova, Perm (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 796 days.

(21) Appl. No.: 17/021,157

(22) Filed: Sep. 15, 2020

(65) Prior Publication Data
US 2021/0121068 A1  Apr. 29, 2021

(30) Foreign Application Priority Data

Oct. 25, 2019 (RU) .................................. 2019134249
Jun. 18, 2020 (KR) ........................ 10-2020-0074450

(51) Int. Cl.
*A61B 5/00* (2006.01)
*G01J 3/42* (2006.01)
(Continued)

(52) U.S. Cl.
CPC .............. *A61B 5/0075* (2013.01); *G01J 3/42* (2013.01); *G01N 21/39* (2013.01); *A61B 5/1455* (2013.01);
(Continued)

(58) Field of Classification Search
None
See application file for complete search history.

(56) References Cited

U.S. PATENT DOCUMENTS 6,816,515 B1  11/2004  Yun et al.
7,505,490 B2  3/2009  Romano et al.
(Continued)

FOREIGN PATENT DOCUMENTS

JP  2012-150253 A  8/2012
JP  2015-106829 A  6/2015
(Continued)

OTHER PUBLICATIONS

Electric heating by Wikipedia pub. online on Sep. 20, 2019 at <https://en.wikipedia.org/w/index.php?title=Electric_heating&oldid=916779875> (Year: 2019).*

(Continued)

*Primary Examiner* — Pascal M Bui Pho
*Assistant Examiner* — Michael S Kellogg
(74) *Attorney, Agent, or Firm* — Sughrue Mion, PLLC

(57) ABSTRACT

A spectrometer may include: a tunable on-chip laser source configured to irradiate a biological tissue with laser radiation; a photodetector configured to receive the laser radiation reflected from the biological tissue; and at least one processor. The tunable on-chip laser source may include: a semiconductor gain chip having a gain bandwidth for operating the tunable on-chip laser source in a predetermined wavelength range; and a plurality of resonator cavities connected between the semiconductor gain chip and the at least one
(Continued)

processor, and configured to perform a coarse high-speed measurement and a fine measurement to measure a spectrum of the laser radiation reflected from the biological tissue.

7 Claims, 13 Drawing Sheets

(51) Int. Cl.
    *G01N 21/39*     (2006.01)
    *A61B 5/1455*     (2006.01)
    *G01J 3/10*     (2006.01)

(52) U.S. Cl.
    CPC ... *G01J 2003/106* (2013.01); *G01J 2003/423* (2013.01)

(56) References Cited

U.S. PATENT DOCUMENTS

| | | | |
|---|---|---|---|
| 7,573,919 | B2 | 8/2009 | Cattelan et al. |
| 8,164,748 | B1 | 4/2012 | Flanders et al. |
| 8,285,368 | B2 | 10/2012 | Chen et al. |
| 9,496,953 | B2 | 11/2016 | Nakagawa et al. |
| 9,651,422 | B2 | 5/2017 | Saptari |
| 9,702,685 | B2 | 7/2017 | Kim et al. |
| 9,739,593 | B2 | 8/2017 | Ha et al. |
| 2008/0220512 | A1 | 9/2008 | Koh et al. |
| 2009/0080882 | A1 | 3/2009 | Cahill |
| 2010/0253935 | A1 | 10/2010 | MacKinnon et al. |
| 2013/0195129 | A1* | 8/2013 | Coleman ............ H01S 5/141 372/20 |
| 2013/0223844 | A1 | 8/2013 | Hwang |
| 2014/0168636 | A1 | 6/2014 | Funamoto |
| 2016/0282640 | A1 | 9/2016 | Guzzon |
| 2020/0069225 | A1 | 3/2020 | Vizbaras et al. |

FOREIGN PATENT DOCUMENTS

| | | | |
|---|---|---|---|
| JP | 2018-200183 A | 12/2018 | |
| KR | 1999-0081342 A | 11/1999 | |
| KR | 2002-0032888 A | 5/2002 | |
| KR | 10-2006-0065723 A | 6/2006 | |
| KR | 10-2013-0127355 A | 11/2013 | |
| KR | 10-2015-0054542 A | 5/2015 | |
| KR | 10-1937393 B1 | 1/2019 | |
| RU | 2008 126 406 A | 1/2010 | |
| RU | 2 649 048 C1 | 3/2018 | |
| WO | 2009/070849 A1 | 6/2009 | |
| WO | WO-2018215388 A1 * | 11/2018 | ........... A61B 5/0002 |

OTHER PUBLICATIONS

Search Report dated Mar. 4, 2020 issued by the Russian Intellectual Property Office in counterpart Russian Application No. 2019134249.
Communication issued Mar. 19, 2021 by the European Patent Office in corresponding European Application No. 20199491.0.
Communication dated Jan. 16, 2025, issued by the Korean Patent Office in Korean Application No. 10-2020-0074450.

* cited by examiner

COARSE MEASUREMENT OF A REFLECTION SPECTRUM OF
THE SAMPLE MEASURED AT HIGH SPEED

FINE MEASUREMENT OF A REFLECTION SPECTRUM OF
THE SAMPLE MEASURED AT HIGH SPEED

SPECTROMETER INCLUDING TUNABLE ON-CHIP LASER AND SPECTRUM MEASUREMENT METHOD

CROSS-REFERENCE TO RELATED APPLICATION(S)

This application claims priority from Russian Patent Application No. 2019134249, filed on Oct. 25, 2019 in the Russian Intellectual Property Office, and Korean Patent Application No. 10-2020-0074450, filed on Jun. 18, 2020 in the Korean Intellectual Property Office, the disclosures of which are incorporated herein by reference in their entireties.

TECHNICAL FIELD

Apparatuses and methods consistent with example embodiments relate to measuring an optical spectrum from a subject to obtain bio information of the subject, and, more specifically, to a spectrometer including a tunable on-chip laser and a spectrum measurement method using the spectrometer.

BACKGROUND

Optical devices for using with spectroscopic purposes are required to possess such feature as sweeping of the light wavelength. This feature can be implemented via using narrow bandwidth tunable light sources such as lasers, or via using wideband light sources such as light emitting diodes (LED) combined with system of optical filters. Both these options imply bulky overall construction of light source system that results in bigger size of the whole spectrometer is difficult to fit into wearable form-factor. Form factor or size is a standard that defines the overall dimensions of a technical product, and describes additional sets of technical parameters of the product, for example, shape.

There are currently three problems.

The first problem is insufficient compactness of the spectrometer. A known spectrometer cannot be worn on the arm as a bracelet. Existing devices designed for this purpose are not compact.

The spectral resolution of commercially available spectroscopic devices intended for use in a wearable form factor does not exceed about 20 nm. Modern important tasks, such as noninvasive detection of a blood glucose levels, require higher spectral resolution, which should be much less than several nanometers.

The second problem is a low spectral resolution of known spectrometers.

When determining the glucose level, it is required to measure the reflection spectrum from the object, this can be realized either as a set of narrow-band light sources, such as a laser, or using a wide-band light source, such as light-emitting diodes, combined by an optical filter system, which implies a fairly large-scale design.

If the spectrum is measured using a set of narrow-band sources, then a set of points is obtained on this spectrum, the distance between said points determines the resolution of the device. For existing devices, the resolution is not high enough, which does not meet the requirements of measuring such a parameter as blood glucose.

The third problem is discrete wavelength sweeping. Such a sweeping is carried out discretely in existing devices with tunable wavelength, i.e. the tuning is performed at some fixed step in each time interval, and the wavelength sweeping, which is carried out continuously and smoothly, is not provided.

Broad-band LED sources in combination with individual optical filters or a set of narrow-band lasers are used for scanning along the wavelength in existing optical spectroscopic devices. These elements are turned on and off in a predetermined sequence necessary for measurements. Such devices do not allow to obtain a continuous scan along the wavelength, which is important to achieve maximum measurement accuracy.

In the related art, a LED based coded source spectrometer includes a plurality of LED light sources that are capable of exhibiting different wavelengths and bandwidths, and the LED light sources are arranged in any convenient manner about a detector module, wherein sample and reference optical paths are distinct from one another. The LED sources are switched in a coded pattern or patterns corresponding to the Hadamard Complement scheme, or to a modified Hadamard Complement scheme. Discrete wavelength sweeping and a low spectral resolution should be mentioned as drawbacks of said spectrometer.

A large number of light emitting diodes are used in the spectrometer and the number of these diodes determines the spectral resolution. If it is necessary to increase the spectral resolution, the number of light sources, i.e. number of diodes should be increased. However, the number of the diodes cannot be increased to infinity, because the device is limited in size.

In the related art, a noninvasive glucose sensor noninvasively measures glucose concentration by measuring a plurality of absorption values using at least one emitter operating at the corresponding plurality of wavelengths through the total optical volume of a sample, and obtaining the glucose concentration from the absorption measurement values.

The noninvasive glucose sensor is configured, for example, as a mall device, attached to a wrist, which people with diabetes can wear to generate continuous and noninvasive measurements of blood glucose levels. The sensor and sensing technique enable measurement of glucose, water, and albumin noninvasively and continuously. The sensor can be implemented as a low power, small size, and low cost device. A vertical cavity surface-emitting laser (VCSEL) is a type of semiconductor laser that can be configured as a tunable emitter. In some embodiments, the emitter can be used in a sensor for monitoring blood glucose levels. Generally, edge-emitting semiconductor lasers have less accuracy and may be less expensive than VCSELs.

In this device, so-called "vixels" are used as light source—light-emitting sources with a vertical resonator, i.e. vertical cavity lasers emitting from the surface. This device does not imply wavelength sweeping, several lasers are used here, and the number of these lasers determines the spectral resolution of the device. In addition, the use of a large number of these lasers is a rather expensive solution.

In the related art, a tunable-laser based spectroscopy system is used to non-invasively measure body water content. One of the important indicators of health is the water content in the body, and therefore the spectroscopy system helps to quantitatively control the level of hydration of the body and determine whether it is necessary to add or reduce water in the body.

The system for assessing a body fluid metric includes a laser configured and arranged to illuminate at least a portion of a body tissue and a single detector in optical communication with the at least a portion of a body tissue. For example, a system may include a tunable laser and/or one or more fixed wavelength lasers. The system, in some embodiments, may include a sensor comprising a first optic fiber having a first end that is configured and arranged to optically communicate with the laser and having a second end that is configured and arranged to optically communicate with a tissue sample; and a second optic fiber having a first end that is configured and arranged to optically communicate with the detector and having a second end that is configured and arranged to optically communicate with a tissue sample. The system may further include a wavelength division multiplexer and/or an optical Switch in optical communication with the laser and the first optic fiber. The system, according to some embodiments, may include a detector comprising a photodiode and/or an optical switch in optical communication with the second optic fiber. The optic fiber (e.g., the first optic fiber and/or the second optic fiber) may comprise a splitter in some embodiments. A sensor, according to some embodiments, may be configured and arranged to be disposable or reusable. A sensor may include a collimator, a star splitter, and/or a beam expander in optical communication with the laser. In some embodiments, the system may exclude a diffraction grating and/or a detector array.

The spectroscopy system in the related art include bulky elements or components that do not fit into a wearable device.

Another spectrometer in the related art includes: a tungsten lamp (being the first light source) which emits light without a peak wavelength in the wavelength range of visible light and having a light amount increasing as the wavelength becomes longer; a violet LED (being the second light source) which emits light having the peak wavelength within the wavelength range of visible light; and a light mixer which mixes light emitted from the respective light sources, i.e. the tungsten lamp and the a violet LED; a light receiving unit (an etalon), which receives light mixed by the light mixer and transmits light contained in the received mixed light and having a particular wavelength; and a measurement control unit that measures the spectral characteristics of the test target light that can pass through the etalon and measures spectral characteristics of the light having passed through the etalon based on the light received by the light receiving unit.

When only the first light source which does not have a peak wavelength within the wavelength range of visible light is used, the light amount within a specific range in the wavelength range of visible light consider ably decreases as explained above. However, the second light source which emits light having the peak wavelength particularly in a shortwave length range (wavelength range where the light amount from the first light source decreases), can effectively compensate for the light amount in the short wavelength range where the light amount from the first light source considerably drops. Accordingly, the measurement accuracy of the spectral characteristics in the wavelength range where the light amount decreases can improve, which contributes to highly accurate measurement of the spectral characteristics.

Discrete wavelength sweeping and a low spectral resolution should be mentioned as drawbacks of said spectrometer. Here, discrete wavelength tuning is performed. Smooth rebuilding is not carried out. There are certain steps that determine the resolution, and rebuilding is carried out with minimal sections, i.e. discretely.

SUMMARY

Example embodiments address at least the above problems and/or disadvantages and other disadvantages not described above. Also, the example embodiments are not required to overcome the disadvantages described above, and may not overcome any of the problems described above.

One or more example embodiments provide spectroscopic measurements with high spectral resolution and continuous wavelength tuning using means compact enough to fit the wearable form factor, while maintaining a low level of energy consumption, said object is achieved by creating a spectrometer based upon a tunable on-chip laser, which is maximal compact so that it can be arranged on an arm in the form of a bracelet, has a high spectral resolution and provides continuous wavelength sweeping carried out smoothly.

The technical effect achieved by one or more example embodiments of the present disclosure is to ensure maximal compactness, i.e. to satisfy the required wearable form factor, to provide a higher performance, that is continuous wavelength sweeping, a higher measurement speed, a high signal-to-noise ratio due to the use of lasers, and a high spectral resolution and an ability to perform coarse and fine (if required) spectrum measurements simultaneously.

According to an aspect of an example embodiment, there is provided a spectrometer including: a tunable on-chip laser source configured to irradiate a biological tissue with laser radiation; a photodetector configured to receive the laser radiation reflected from the biological tissue; and at least one processor, wherein the tunable on-chip laser source may include: a semiconductor gain chip having a gain bandwidth for operating the tunable on-chip laser source in a predetermined wavelength range; a plurality of resonator cavities connected between the semiconductor gain chip and the at least one processor, and comprising a first resonator cavity and a second resonator cavity. Each of the plurality of resonator cavities may include a waveguide and a plurality of tunable filters to generate lights having different wavelengths in accordance with parameters of the plurality of tunable filters of each of the plurality of resonator cavities, as the laser radiation to be emitted to the biological tissue. The first resonator cavity may include a first tunable filter among the plurality of tunable filters, and may be configured to perform a coarse high-speed measurement to measure a spectrum of the laser radiation reflected from the biological tissue while the biological tissue is irradiated by the laser radiation generated by the first tunable filter of the first resonator cavity. The second resonator cavity may include a second tunable filter among the plurality of tunable filters, and may be configured to perform a fine measurement to measure the spectrum of the laser radiation reflected from the biological tissue while the biological tissue is irradiated by the laser radiation generated by the second tunable filter.

The waveguide of each of the plurality of resonator cavities may be ended with a Sagnac mirror providing a feedback loop between each of the plurality of resonator cavities and the semiconductor gain chip.

The spectrometer may further include: metal heating elements located in the plurality of resonator cavities and configured to receive voltage from an external source, and a thermo-optic control circuit configured to tune a wavelength of the plurality of resonator cavities by applying the voltage to the metal heating elements.

The spectrometer may further include: a plurality of electro-optic control circuits configured to tune a wavelength of the plurality of resonator cavities by applying an electric field to the plurality of resonator cavities to change an effective refractive index of the plurality of resonator cavities and a transmission spectrum of the laser radiation emitted from the spectrometer.

The spectrometer may further include: a plurality of acousto-optic control circuits, configured to tune a wavelength of the plurality of resonator cavities, by exposing the plurality of resonator cavities to ultrasonic vibrations from an external source.

The semiconductor gain chip having the gain bandwidth for operating the tunable on-chip laser source in the predetermined wavelength range may be a first semiconductor gain chip having a first gain bandwidth for operating the tunable on-chip laser source in the predetermined wavelength range. The spectrometer may include an array of semiconductor gain chips having different gain bandwidths to provide sweeping along a wavelength in an extended wavelength range that is wider than the predetermined wavelength range. The array of semiconductor gain chips having the different gain bandwidths may include the first semiconductor gain chip having the first gain bandwidth.

The spectrometer may further include a modulator configured to control the gain bandwidth of the semiconductor gain chip.

The spectrometer may further include a feedback control circuit and wavelength calibration circuits to calibrate a wavelength of the spectrometer in real time.

The spectrometer may further include a splitter configured to connect the semiconductor gain chip to the plurality of resonator cavities.

The first resonator cavity may include a first mirror that is paired with the first tunable filter, and the second resonator cavity may include a second mirror that is paired with the second tunable filter.

According to an aspect of another example embodiment, there is provided a method of obtaining bio information by using a spectrometer including a plurality of resonator cavities. The plurality of resonator cavities may include a first resonator cavity and a second resonator cavity. The method may include: irradiating a biological tissue with a first laser radiation generated by a first tunable filter of the first resonator cavity, while the first resonator cavity performs a coarse high-speed measurement to measure a spectrum of the first laser radiation reflected from the biological tissue; irradiating the biological tissue with a second laser radiation generated by a second tunable filter of the second resonator cavity while the second resonator cavity performs a fine low-speed measurement to measure a spectrum of the second laser radiation reflected from the biological tissue; and obtain the bio information based on the coarse high-speed measurement and the fine low-speed measurement.

The method may further include: tuning an irradiation wavelength in a waveguide of the first resonator cavity by thermo-optical tuning a wavelength of the first and the second tunable filters by heating the waveguide in the first resonator cavity.

The method may further include: electro-optical tuning a wavelength of the first and the second tunable filters by changing a refractive index of a waveguide of the first resonator cavity by applying an external electric field to the waveguide.

The method may further include: acousto-optic tuning a wavelength of the first and the second tunable optical filters by applying ultrasonic vibrations to a waveguide of the first resonator cavity to change an effective transmission spectrum of the waveguide of the first resonator cavity.

A spectrometer according to example embodiments may provide the following advantages:
  simplifying and miniaturizing the whole optical scheme, where the gain-chip is the biggest element;
  sweeping wavelengths $\lambda_1$ and $\lambda_2$ simultaneously and independently which gives high flexibility in obtaining spectrum of a target biological tissue, wherein the sweeping is performed via changing transmittance of tunable filters;
  using lesser gain-chips if several wavelengths are required, that results in decreasing power consumption and dissipation within the whole device;
  covering an extended range of wavelengths, e.g. 1500-1800 nm, it is important for blood glucose measurements;
  providing a possibility of implementing complex modulation of output power, which is important for communication systems;
  providing higher accuracy of wavelength control due to real-time calibration.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
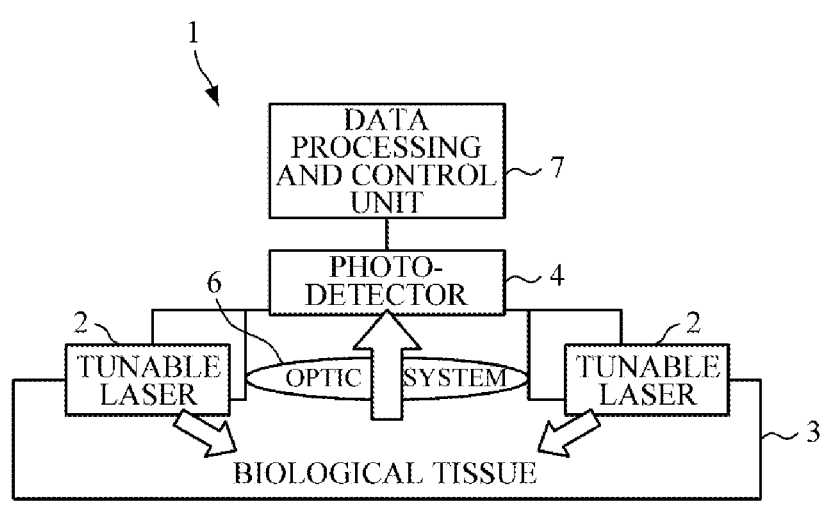
FIG. 1 is a diagram of a spectrometer according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 illustrates a diagram of a spectrometer according to an example embodiment.

A spectrometer 1 shown in FIG. 1 may include a laser source 2 configured to irradiate a biological tissue 3 with laser radiation. The spectrometer 1 may include a photodetector 4 configured to receive radiation 5 reflected from the biological tissue 3 and passed through an optical system 6 providing collimation of the incident radiation and directing the incident radiation to the photodetector 4; and a control and photodetector data processing unit (e.g., a processor) 7.

Figure 2A:
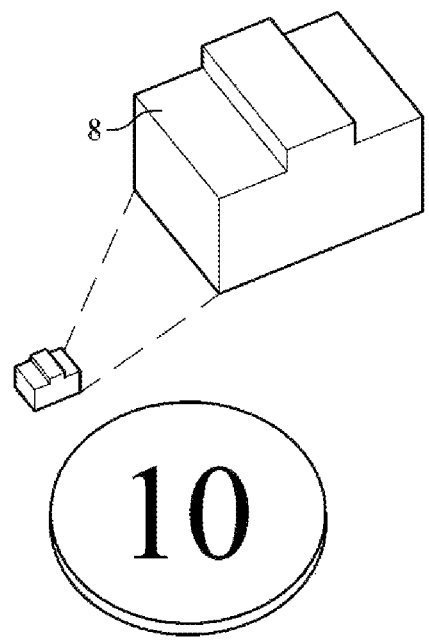
FIG. 2A is a top view of a gain chip according to an example embodiment, which is placed next to a coin.
Figure 2B:
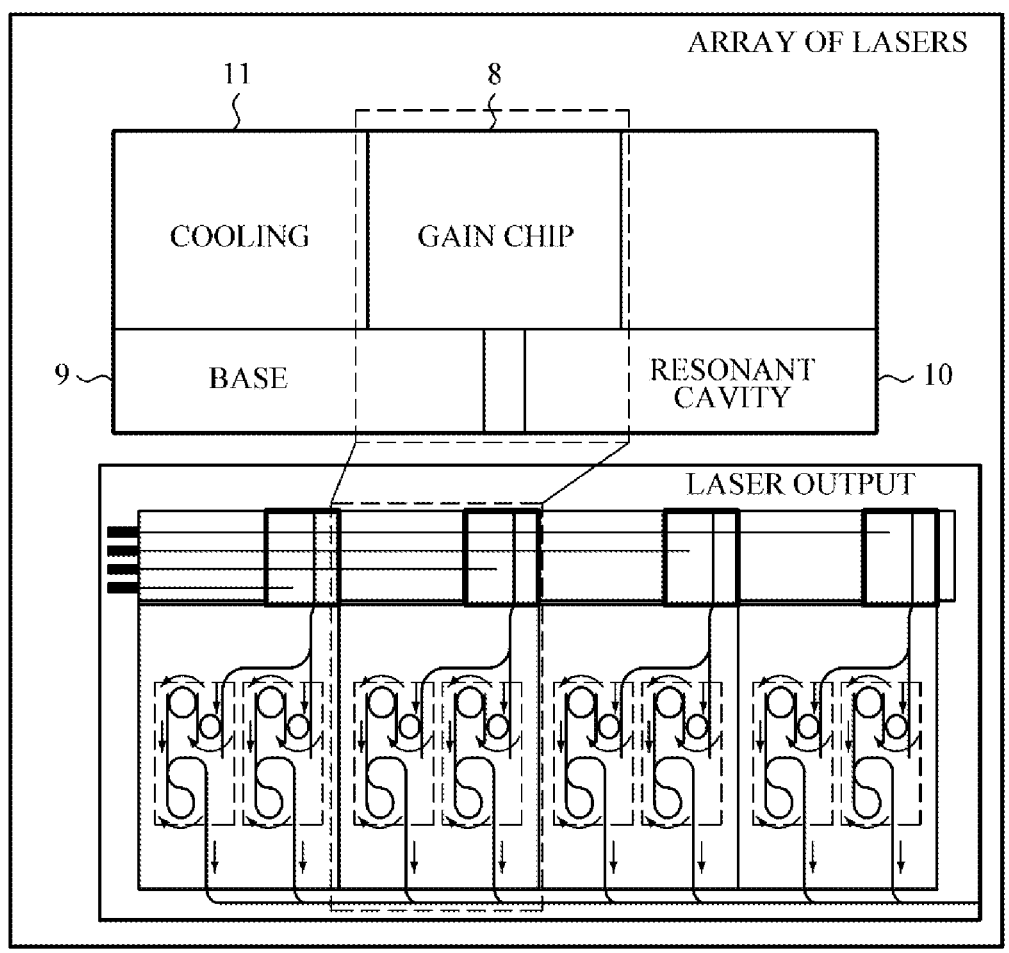
FIG. 2B is a diagram of a tunable on-chip laser including a plurality of resonators according to an example embodiment.

FIG. 2A shows a top view of a semiconductor gain chip 8 included in the spectrometer 1, and FIG. 2B illustrates a diagram of a tunable on-chip laser that may be used as the laser source 2 shown in FIG. 1. The tunable on-chip laser may include an array of lasers, and the semiconductor gain chip 8 combined with a photonic chip substrate (or a base) 9 and a cooling system 11. The semiconductor gain chip 8 is connected to one or more resonator cavities 10. The resonator cavities 10 may be also referred to as resonators (including cavities therein).

Figure 3:
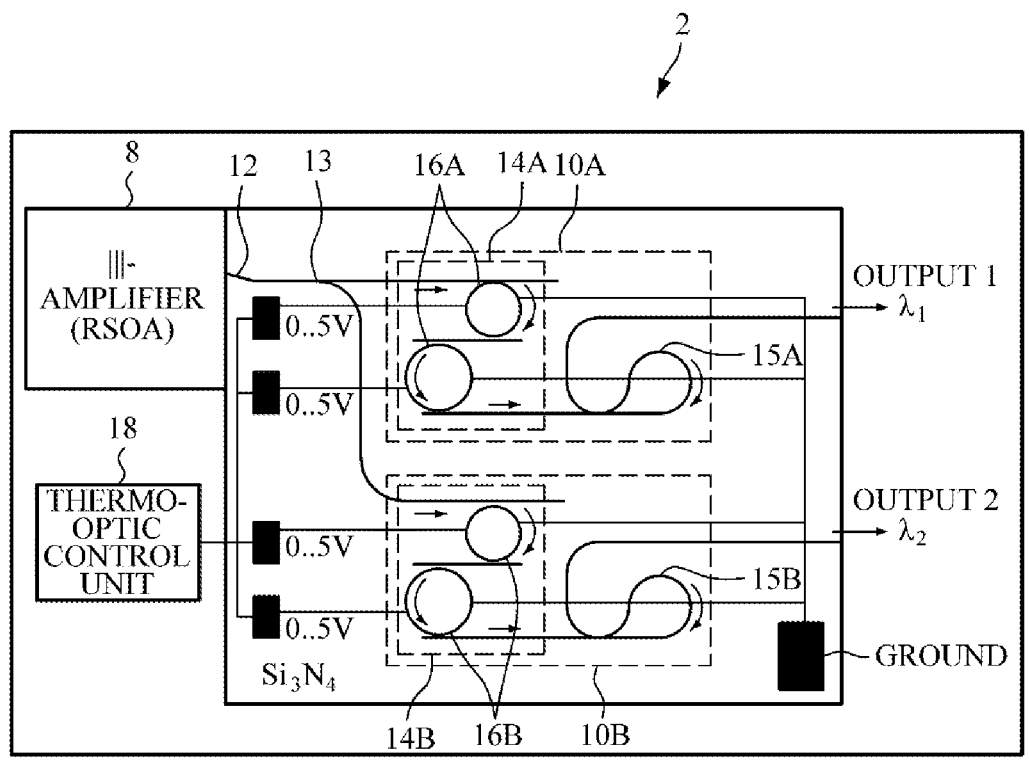
FIG. 3 is a detailed scheme of a tunable on-chip laser including two resonators according to an example embodiment.
Figure 4:
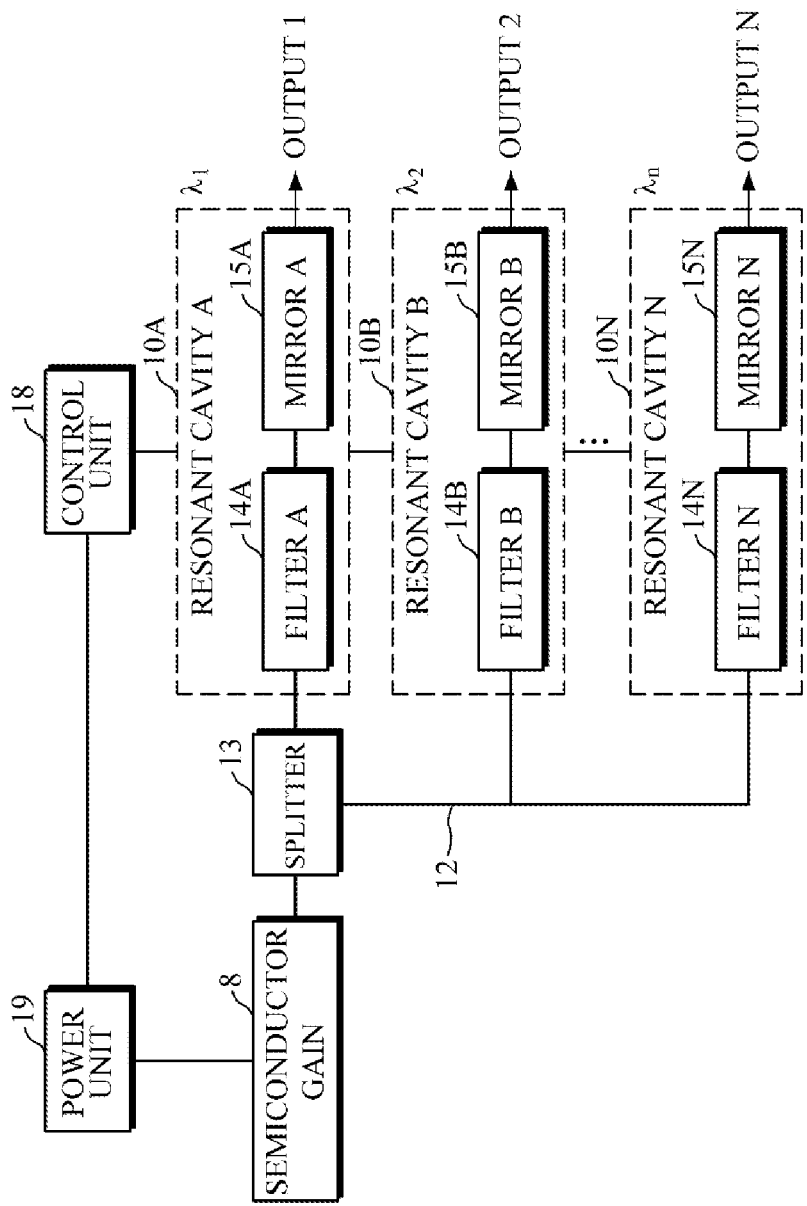
FIG. 4 is a scheme of a tunable on-chip laser according to an example embodiment.

FIG. 3 shows a detailed scheme of a tunable on-chip laser including two resonator cavities 16A and 16B. FIG. 4 shows a scheme of a tunable on-chip laser including N resonator cavities 10A, 10B, and 10N. The semiconductor gain chip is characterized by its own gain bandwidth for operation of a tunable on-chip laser in a predetermined wavelength range and is connected by waveguides 12 as shown in FIGS. 3 and 4. The waveguides 12 are split through a splitter 13, and connected to one or more resonator cavities 10A, 10B, and 10N. The resonator cavities 10A, 10B and 10N are connected to a control unit 18 and a power unit (e.g., a power supply) 19. The control unit 18 may include or correspond to the control and photodetector data processing unit 7, or may be provided separately from the control and photodetector data processing unit 7 and may have a circuit structure. The control unit 18 may be also referred to as a control circuit.

Each of the resonator cavities 10A, 10B, and 10N may include a waveguide 12 and a tunable filter. The resonator cavity 10A may include a tunable filter 14A and a mirror 15A, the resonator cavity 10B may include a tunable filter 14B and a mirror 15B, and the resonator cavity 10N may include a tunable filter 14N and a mirror 15N.

Each of the resonator cavities 10A, 10B, and 10N includes two cascade microresonator cavities 16A and 16B, as shown in FIG. 3, to ensure that lights (e.g., OUTPUT 1, OUTPUT 2, and OUTPUT N) generated by the laser source 2 have different wavelengths λ1, λ2, . . . λn in accordance with parameters of the tunable filters 14A, 14B, and 14C included in the resonator cavities 10A, 10B, and 10N, respectively.

In accordance with example embodiments, the spectrometer 1 may include two resonator cavities 10A and 10B as shown in FIG. 3, or may include more than two resonator cavities 10A, 10B, and 10C as shown in FIG. 4.

The tunable filter 14A of said resonator cavity 10A is configured for coarse high-speed measurement of a reflection spectrum R(λ) of a target (e.g., the biological tissue 3) that is obtained by collecting a light generated by the resonator cavity 10A and then reflected from the target, and the tunable filter 14B of said resonator cavity 10B is configured for fine low-speed measurement of the reflection spectrum R(λ) of the target, that is obtained by collecting a light generated by resonator cavity 10B and then reflected from the target.

The waveguide 12 of each of the resonator cavities 10A, 10B, and 10C is ended with a corresponding Sagnac mirror 15A, 15B, and 15N, thus providing a feedback loop between the resonator cavity 10A, 10B, and 10C and the semiconductor gain chip 8.

The splitter 13 divides the energy of one semiconductor gain chip 8 into two or more resonator cavities 10A, 10B, and 10C. The main effect of this implementation is the simplicity of manufacture. Since the resonator cavities 10A, 10B, and 10C are manufactured integrally, using silicon on insulator (SOI) technology, or silicon nitride on insulator using photolithography methods, the manufacture of this scheme on an industrial scale can be very simple.

As shown in FIGS. 3 and 4, the laser source 2 may include metal heating elements located on the surface of one or more tunable filters 14A, 14B, and 14C as part of the resonator cavities 10A, 10B, and 10C, and configured to receive voltage from the power unit (e.g., an external source) 19.

Figure 6:
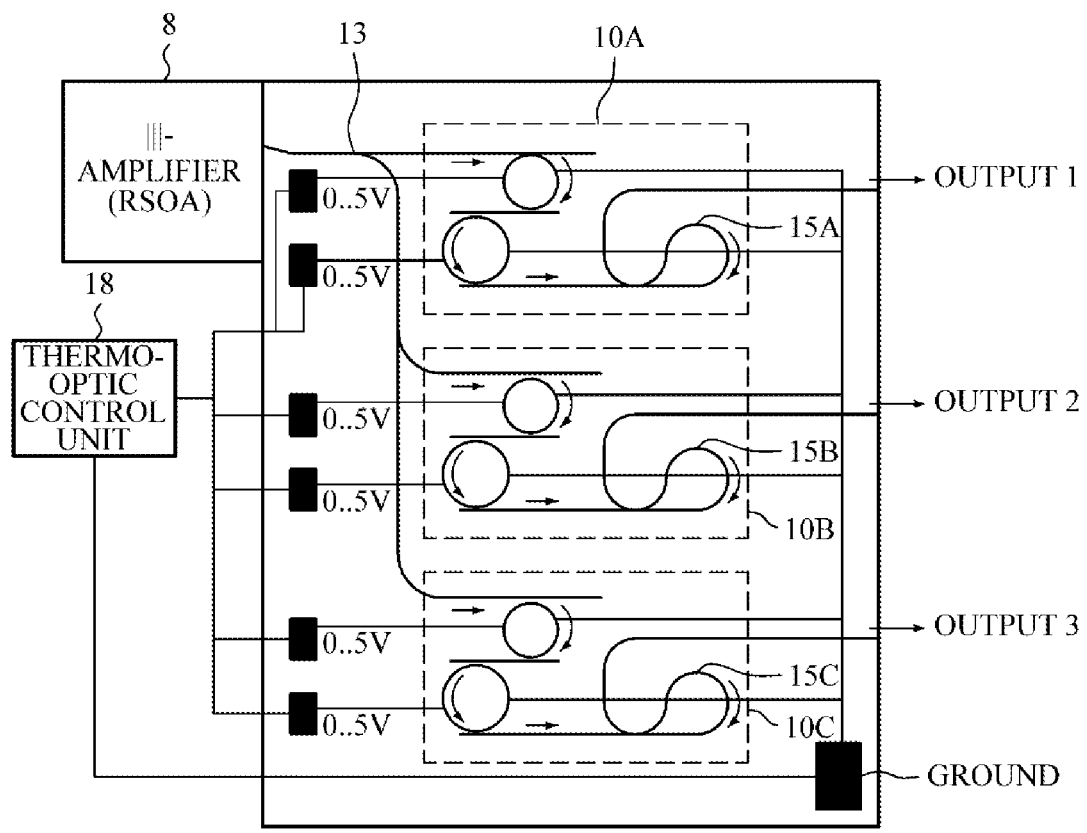
FIG. 6 is a scheme of a tunable on-chip laser including thermo-optic resonator control units, according to an example embodiment.

In accordance with example embodiments, FIGS. 3 and 6 show that the control unit 18 of the spectrometer 1 may include a thermo-optic control unit (e.g., a thermo-optic control circuit) for controlling the metal heating elements that are configured to tune the wavelength of the resonator cavities 10A, 10B, and 10C, wherein the wavelength tuning is performed by applying voltage to the metal heating elements.

Figure 7:
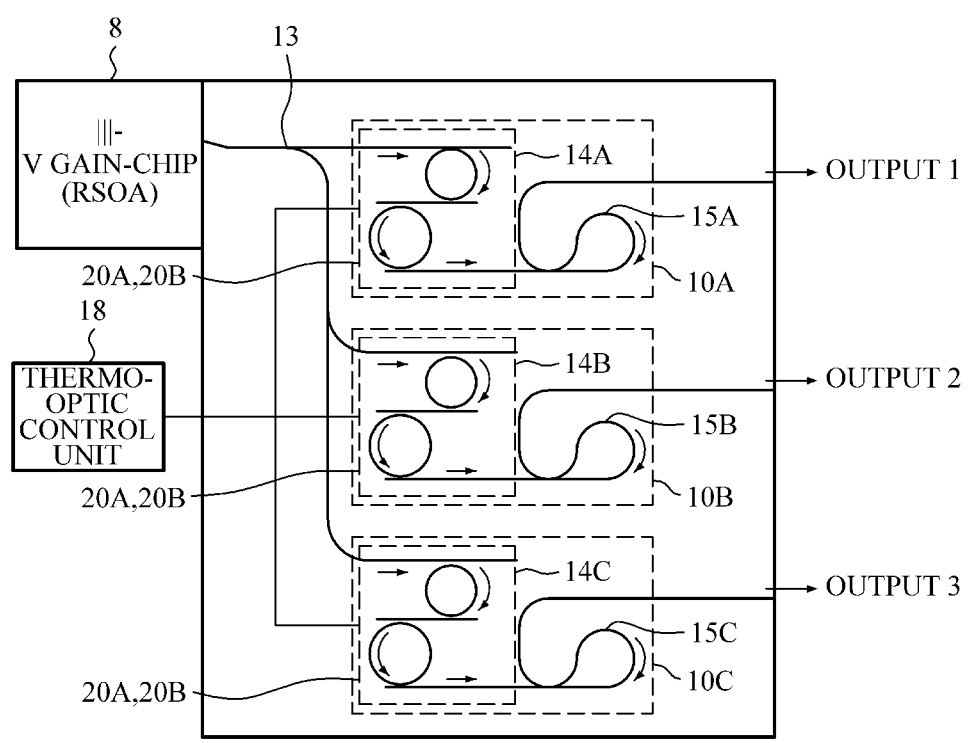
FIG. 7 is a scheme of a tunable on-chip laser including electro-optics/acousto-optic resonator control units, according to an example embodiment.

According to another example, embodiment, the spectrometer 1 shown in FIG. 7 includes electro-optic control units (e.g., an electro-optic control circuits) 20A in accordance with the number of the resonator cavities, configured to tune the wavelength of the resonator cavities by applying an electric field to the resonator cavities, wherein a change of the electric field amends the effective refractive index of the resonator cavities and the transmission spectrum, accordingly, which ensures tuning of the wavelength.

According to another example, the spectrometer 1 shown in FIG. 7 may include comprises acousto-optic control units (e.g., acousto-optic control circuits) 20B in accordance with the number of the resonator cavities, configured to tune the wavelength of the resonator cavities, wherein the wavelength is tuned by exposing the resonator cavities to ultrasonic vibrations from an external source, wherein the parameters of the ultrasonic vibrations determine the transmittance spectrum, which ensures tuning of the wavelength.

Figure 8:
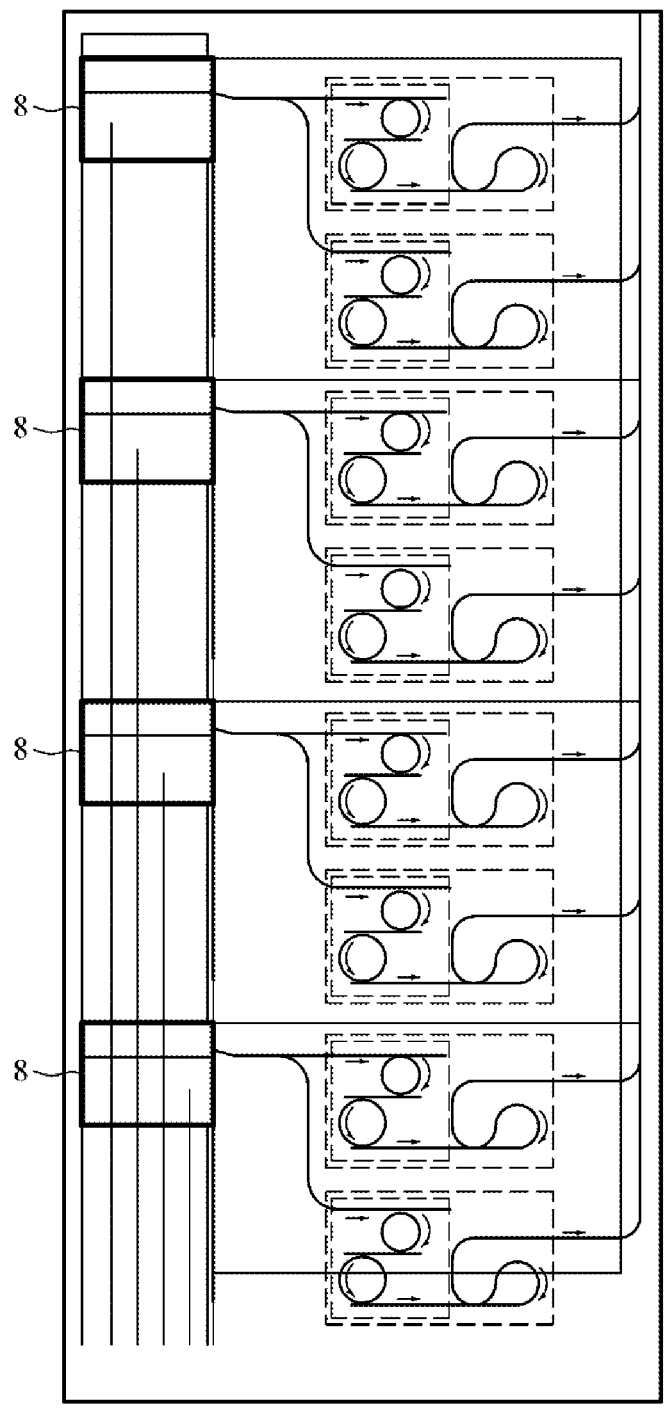
FIG. 8 is an array of tunable on-chip lasers on a single base, according to an example embodiment.

According to another embodiment, the spectrometer 1 shown in FIG. 8 includes an array of semiconductor gain chips 8 with different gain bandwidths to provide sweeping along the wavelength in the extended wavelength range, for example, 1500-1800 nm.

As a rule, any semiconductor amplifier has its own gain bandwidth and the laser cannot operate outside this bandwidth. This bandwidth is limited. If it is necessary to measure the spectrum in a bandwidth that exceeds the gain bandwidth of the semiconductor gain chip, another semiconductor gain chip with a different gain bandwidth should be used. Combining several tunable lasers, each of which is based on its own semiconductor gain chip with its own bandwidth it is possible to combine their bandwidths in a simple way, i.e. dock or attach one to the other to eventually cover the entire range.

Figure 9:
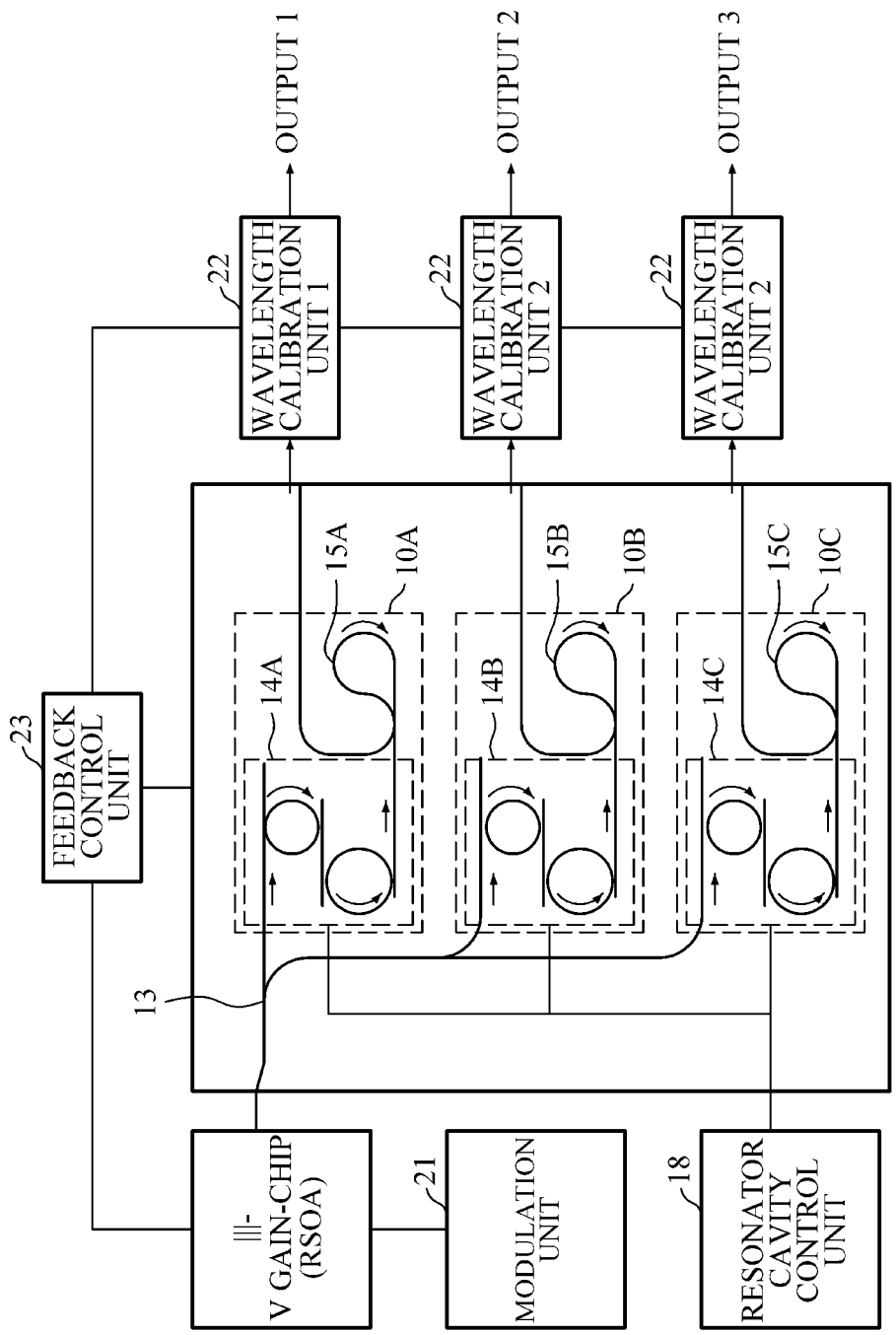
FIG. 9 is a scheme of a tunable on-chip laser comprising a real-time wavelength calibration unit of the spectrometer, according to an example embodiment.

According to another embodiment, the spectrometer 1 shown in FIG. 9 includes the control unit 18 configured to control the resonator cavities, and a modulation unit (or a modulation module) 21 configured to control a gain bandwidth of a semiconductor gain chip.

According to another embodiment, the spectrometer 1 shown in FIG. 9 includes a feedback control unit 23 and wavelength calibration units 22 for real-time calibrating the spectrometer wavelength.

A method of measurement of a reflected radiation from a biological object by use of the spectrometer includes the following operations.

Figure 10:
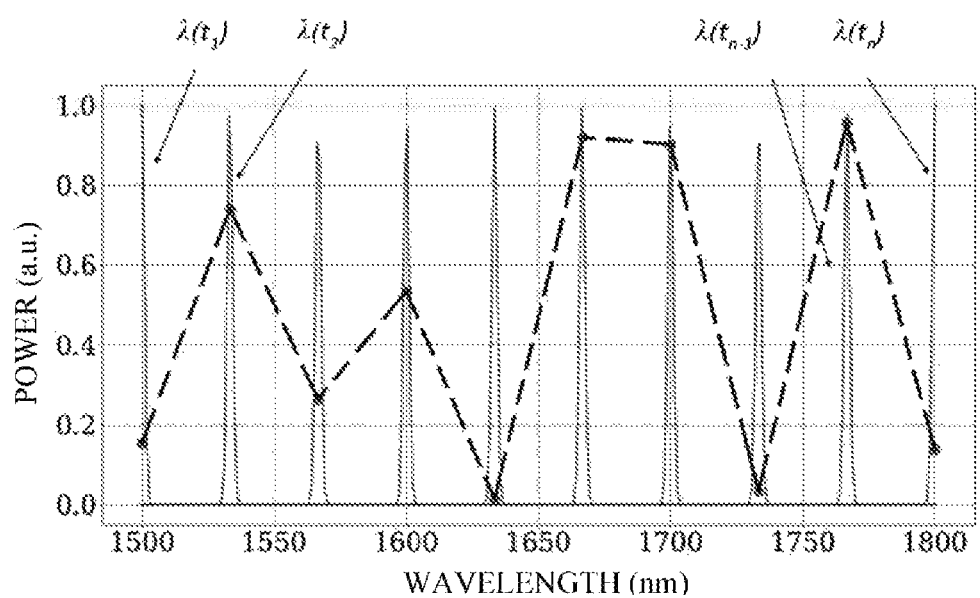
FIG. 10 is a sample reflection optical spectrum obtained using a spectrometer with a laser source consisting of an array of tunable on-chip lasers, according to an example embodiment.

The spectrometer can be fixed on a patient's arm, due to its compact size. The biological tissue is irradiated with laser radiation generated by two or more resonator cavities 10A, 10B, and 10C, wherein the tunable filter 14A of the resonator 10A is configured for coarse high-speed measurement of the reflectance spectrum R (λ) (FIG. 10) of a target (e.g., the biological tissue) as shown in FIG. 10, when the target is irradiated with light generated by the resonator cavity 10A shown in FIG. 3.

The method may include an operation of performing a coarse and high speed measurement of the reflectance spectrum R(λ) of the target by light generated within the tunable filter 14A of one or more resonator cavities 10A, 10B, and 10C by tuning the wavelength of the source by changing the transmittance of the tunable filter 14A of the resonator cavity 10 (see FIG. 3).

Figure 11:
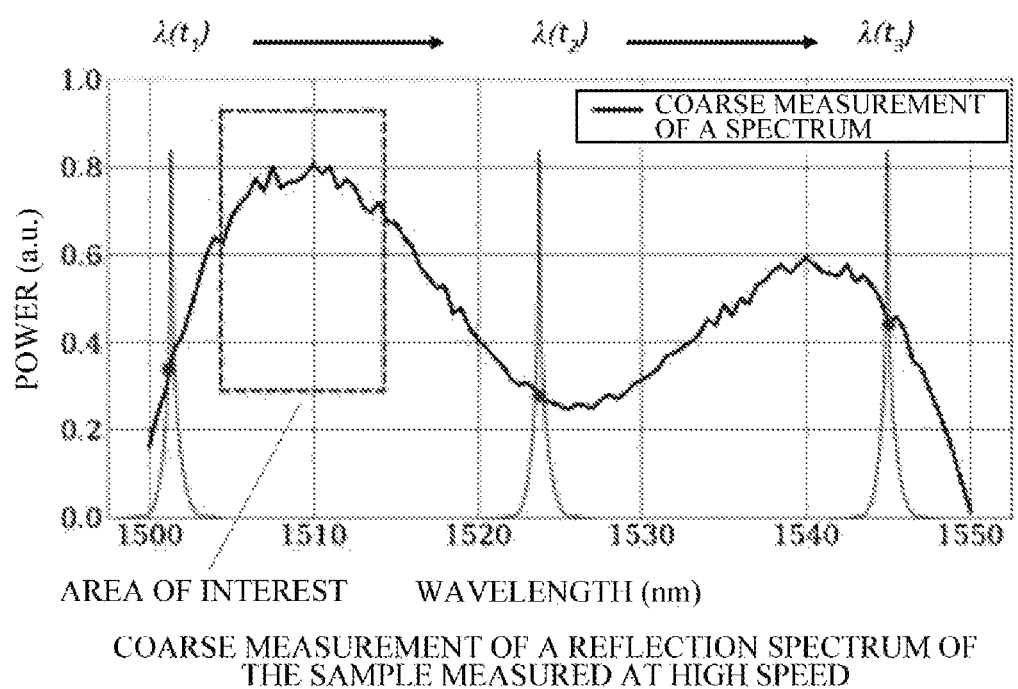
FIG. 11 is a sample reflection optical spectrum of coarse high-speed measurement, according to an example embodiment.
Figure 12:
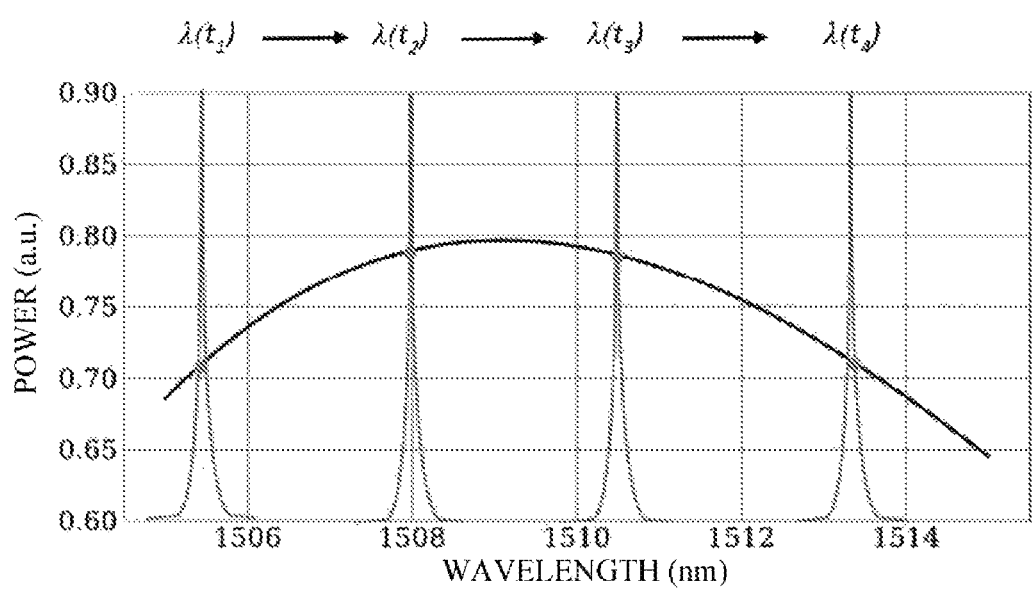
FIG. 12 is a sample reflection optical spectrum of fine low-speed measurement in an area of interest (B), according to an example embodiment.

Then the resulting reflectance spectrum of R (λ) is analyzed and the areas of interest to identify artifacts are determined. The area of interest may be, for example, a portion of the spectrum (a rectangle, shown by a dashed line) of the source containing a sharp peak, as show in FIG. 11.

In addition, the fine low-speed measurements of the reflectance spectrum of the target are performed in the areas of interest, during irradiation generated by the other resonator 10B using tunable filter 14B.

Tuning the irradiation wavelength in the waveguide of the resonator cavity is performed by thermo-optical tuning the wavelength of the tunable optical filters A and B by heating the waveguide in the resonator cavity, wherein the wavelength of the source changes from a smaller value to a larger one, wherein the filtering ability is determined by the refractive index of the material from which the waveguides are made.

According to another embodiment, electro-optical tuning the wavelength of the tunable optical filters A and B is carried out by changing the refractive index of the waveguide of the resonator by applying an external electric field to the waveguide, wherein the wavelength changes from a smaller value to a larger one, and the filtering ability is determined by the refractive index of the material from which the waveguides are made.

According to another embodiment, acousto-optic tuning the wavelength of the waveguide by acousto-optic tuning the wavelength of the tunable optical filters A and B is carried out by changing the transmission spectrum of the waveguide of the resonator cavity, carried out by applying ultrasonic vibrations to the waveguide, wherein the wavelength changes from a smaller value to a larger one, and the filtering ability is determined by refractive index of the material from which the waveguides are made.

Fine tuning along the wavelength is carried out using two microresonator cavities 16A and 16B (FIG. 3) of each of the tunable filters 14A and 14B, operating using the Vernier effect.

This effect is expressed in a significant increase in the range of resonator tuning due to the cascade arrangement of two microresonator cavities 16A, 16B that have different transmission radiation spectrum.

If the distance between the transmission peaks (and, accordingly, the tuning range of the wavelength of the transmitted optical radiation) of the first microresonator cavity is defined as FSR1 and the second microresonator cavity as FSR2, then the tuning range Δ of the resonator cavity consisting of two microresonator cavities, is determined according to the expression $$\Delta = \frac{FSR1 * FSR2}{|FSR1 - FSR2|}$$

that can significantly exceed the values of FSR1 and FSR2.

As indicated above, if it is necessary to measure the spectrum in a bandwidth that exceeds the gain band of the semiconductor gain chip, another semiconductor gain chip with a different gain bandwidth is used. By combining several tunable lasers, each of which is based on its own semiconductor gain chip having own bandwidth, it is possible to simply combine their bands, i.e. dock or attach one to the other to eventually cover the entire range.

Figure 5:
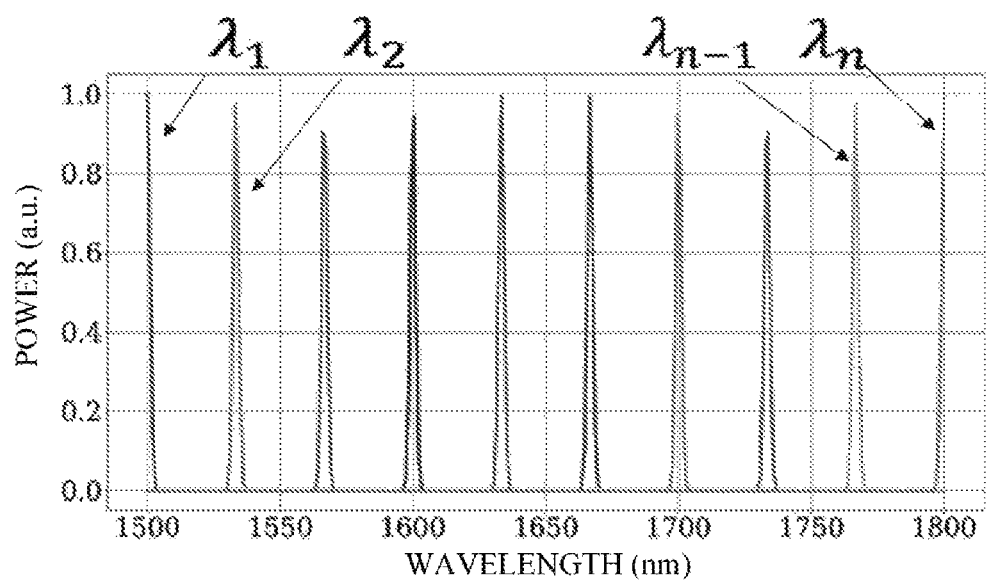
FIG. 5 is a laser source spectrum of a spectrometer, based on array of tunable on-chip lasers, according to an example embodiment.

FIG. 5 shows a certain reference spectrum based on an array of tunable lasers.

At an initial time, the emission spectrum is a set of narrow bandwidths covering the range of from 1500 to 1800 nm. This range is determined in accordance with the object of study. If biological objects should be measured, for example, the glucose content in human tissues, it is necessary to measure the spectrum in this range, and therefore, it may be impossible to make said measurements by using one semiconductor gain chip that covers approximately 50 nm. It will be necessary to use several semiconductor amplifiers.

FIG. 10 shows a reflectance spectrum from the object, which results by using an array of tunable lasers. As a result, a curve is obtained on which each point corresponds to the reflectance spectrum of the wavelength from the object.

The solid line shows the spectrum of the source, and the dashed line shows the reflectance spectrum of the object, for example, from the biological tissue. Thus, it is possible to obtain a very coarse spectrum, i.e. the number of wavelengths corresponds to the number of points, this is a broken curve. This curve may not be very informative at the initial stage, but it allows to estimate the time and areas of interest that are important for more accurate and fine measurement in the future.

The function of the resonator cavity is indicated below:
the resonator cavity provides feedback, i.e. a part of the radiation passing along the waveguide is sent back for amplification;
the resonator cavity provides filtering of the radiation.

Theoretically, any optical filter or a filter of other kind can perform this function.

When a radiation having two different wavelengths λ1 and λ2 is generated simultaneously, the configuration of the spectrometer according to example embodiments allows, firstly, to significantly reduce the size of the entire circuit, since the biggest element is a semiconductor gain chip that is much smaller than a coin. When two different wavelengths are obtained at the output of the resonant cavity by using one gain chip, the circuit is two times smaller compared to a circuit with two semiconductor gain chips that also provides two different wavelengths. However, the energy of one semiconductor gain chip cannot be shared infinitely.

Further, such a scheme according to example embodiments makes it possible to implement the spectrum measuring method by simultaneously tuning two different wavelengths by using a predetermined algorithm.

Thus, the selective measurement of the spectrum is carried out. Two spectrum measurement modes, i.e. coarse and fine measurements are directly related to the use of two wavelengths obtained from a single semiconductor gain chip. Since two wavelengths are generated, it is possible to carry out a coarse measurement for one wavelength, and a file measurement for the second wavelength.

This is carried out in the following way. At the initial moment, by using one filter and one resonator cavity based on the Vernier effect, a tuning of the wavelength is performed, i.e. the source wavelength varies from shorter to greater with the maximum possible permissible speed. However, the higher the speed, the lower the resolution and the lower the noise signal. In this case, a coarse reflectance spectrum from the object is obtained. The coarse reflectance spectrum is a subject to fluctuations, it can be noisy, since the measurement is carried out very quickly. In this case, a relatively small amount of energy is detected at each moment of time.

After the coarse measurement of the spectrum has been carried out, the resulting curve is analyzed in order to fine the areas of interest that are very important.

When measuring glucose, the spectrum as such is not as informative as its particular parts. This is especially true when the spectrum is used to determine a relative change in glucose or any chemical substance. That is, a relative spectrum measurement may be very important. In this case, it will be necessary to analyze some parts of the spectrum, i.e. how said parts change.

The next step is to perform fine measurement of the areas of interest. For this, the fine measurement mode using the second wavelength is used. That is the parameters of the second resonator cavity is changed in such a way that the wavelength tuning is carried out with a low speed, but not in the entire area, but in the area of interest only.

First, performing a high speed scanning by using a single filter, determining the part of the spectrum being the area of interest, and performing a low speed scanning with the second wavelength.

The advantage of using two wavelengths is as follows. The filtering ability of the optical filters is determined by the temperature dependence of the effective refractive index of the material from which the optical filters are made. Tuning is carried out by heating these resonator cavities. Heating is an inertial process; to heat special metal contacts is much easier than to cool them, and especially in a wearable device, that does not include special active cooling systems. Due to the presence of two separate filter sets with two radiation sources it is possible to provide heating of one resonator cavity, coarse tuning, and then fine tuning by heating the second resonator cavity. It is not necessary to cool the first resonator cavity, wait a certain time for cooling sufficiently in order to carry out tuning once more. In this case, the efficiency and performance of the entire device is increased. The main advantage is that, using two sources, it is not necessary to cool each of them, it is possible to scan twice, by using the first and then second, heating the first and second alternately.

In the second case, the turning of microresonator cavities can be achieved not only with a change in temperature, i.e. by heating, but also by using of various electro-optic effects. In a case in which various materials having a significant electro-optic effect (not ordinary silicon) are used for producing microresonator cavities, i.e. by changing the effective refractive index depending on the applied external electromagnetic field, for example, lithium niobate, it is possible not to change the temperature but to change the applied electromagnetic field.

In a case in which the wavelength calibration unit 22 is used, the operation is as follows.

Each of the radiation sources generates light that enters the calibration unit 22. The calibration unit 22 determines whether the generated wavelength corresponds to that embedded in the control algorithm of the resonator cavity 10A, 10B, or 10C. Turning is carried out on the assumption that there is a certain relationship between the control signal and the wavelength of the resulting radiation.

However, this dependence is subject to external interference. In a case in which the external interference is a temperature, there may be effects associated with additional heating of the entire substrate on which the gain chip is fixed. The wavelength may differ from the desired, i.e. there is a difference between the true and the required wavelength. To compensate this effect, an additional wavelength calibration module is used that is combined with the feedback module of the power supply of the semiconductor gain chip.

Comparing the wavelength and receiving a signal of difference between the true and the required wavelength, a feedback signal is generated and the power of the semiconductor gain chip is changed in order to reduce the signal and change the required wavelength.

Spectrometer including a tunable on-chip laser is used as wearable healthcare sensor primarily to perform: non-invasive blood glucose measurements; non-invasive blood oxygenation level and blood pressure value measurements; non-invasive underskin fat level measurements; non-invasive skin conditions assessment; non-invasive skin moisturization level assessment; food quality assessment; medication quality control; measurements of clothes dirtiness required for smart washing machines; bottled water quality assessment.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectrometer comprising:
   a tunable on-chip laser source configured to irradiate a biological tissue with laser radiation;
   a photodetector configured to receive the laser radiation reflected from the biological tissue; and
   at least one processor;
   wherein the tunable on-chip laser source comprises:
   a semiconductor gain chip having a gain bandwidth for operating the tunable on-chip laser source in a predetermined wavelength range;
   a plurality of resonator cavities connected between the semiconductor gain chip and the at least one processor, and comprising a first resonator cavity configured to radiate a light of a first wavelength band and a second resonator cavity configured to radiate a light of a second wavelength band;

wherein the first resonator cavity comprises:
 a first tunable filter that comprises at least two cascaded micro-resonator cavities; and
 a first mirror that provides a feedback loop between the first resonator cavity and the semiconductor gain chip, and wherein the second resonator cavity comprises:
 a second tunable filter that comprises at least two cascaded micro-resonator cavities; and
 a second mirror that provides a feedback loop between the second resonator cavity and the semiconductor gain chip, wherein the at least one processor is further configured to control the photodetector to;
 measure, during a first measurement step, a spectrum of the laser radiation reflected from the biological tissue at a first wavelength interval within a first wavelength range while the biological tissue is irradiated by the laser radiation generated by the first tunable filter,
 select a second wavelength range that is narrower than the first wavelength range and includes only a greatest peak intensity point from a plurality of peak intensity points of a spectrum within the first wavelength range, and
 during a second measurement step subsequent to the first measurement step, measure the spectrum of the laser radiation reflected from the biological tissue at a second wavelength interval within the second wavelength range, while the biological tissue is irradiated by the laser radiation generated by the second tunable filter, and wherein the second wavelength interval is narrower than the first wavelength interval.

2. The spectrometer according to claim 1, wherein the tunable on-chip laser source further comprises a waveguide that connects the semiconductor gain chip to each of the plurality of resonator cavities.

3. The spectrometer according to claim 1, comprising
 a plurality of metal heating elements located in the plurality of resonator cavities and configured to receive voltage from an external source, and
 a thermo-optic control circuit configured to tune a wavelength of the plurality of resonator cavities by applying the voltage to the plurality of metal heating elements.

4. The spectrometer according to claim 1, further comprising
 a plurality of electro-optic control circuits configured to tune a wavelength of the plurality of resonator cavities by applying an electric field to the plurality of resonator cavities to change an effective refractive index of the plurality of resonator cavities and a transmission spectrum of the laser radiation emitted from the spectrometer.

5. The spectrometer according to claim 1, further comprising
 a plurality of acousto-optic control circuits, configured to tune a wavelength of the plurality of resonator cavities, by exposing the plurality of resonator cavities to ultrasonic vibrations from an external source.

6. The spectrometer according to claim 1, wherein the semiconductor gain chip having the gain bandwidth for operating the tunable on-chip laser source in the predetermined wavelength range is a first semiconductor gain chip having a first gain bandwidth for operating the tunable on-chip laser source in the predetermined wavelength range,
 wherein the spectrometer comprises an array of semiconductor gain chips having different gain bandwidths to provide sweeping along a wavelength in an extended wavelength range that is wider than the predetermined wavelength range, and
 wherein the array of semiconductor gain chips having the different gain bandwidths comprises the first semiconductor gain chip having the first gain bandwidth.

7. The spectrometer according to claim 1, further comprising a splitter configured to split a waveguide that extends from the semiconductor gain chip into a plurality of waveguides that are connected to the plurality of resonator cavities.

* * * * *